United States Patent [19]
Ruddy et al.

[11] Patent Number: 5,539,788
[45] Date of Patent: Jul. 23, 1996

[54] PROMPT GAMMA NEUTRON ACTIVATION ANALYSIS SYSTEM

[75] Inventors: Frank H. Ruddy, Monroeville; Thomas V. Congedo, Pittsburgh; David C. Grant, Gibsonia; Edward J. Lahoda, Edgewood Borough; Joseph L. Gonzalez, White Oak Boro; John G. Seidel, McCandless; John Bartko, State College; David F. McLaughlin, Oakmont, all of Pa.

[73] Assignee: Westinghouse Electric Corporation, Pittsburgh, Pa.

[21] Appl. No.: 958,215

[22] Filed: Oct. 8, 1992

[51] Int. Cl.$^6$ .................................................. G21G 1/06
[52] U.S. Cl. ...................... 376/159; 376/160; 250/253; 250/390.04; 250/390.12
[58] Field of Search ........................ 376/159, 160–166; 250/390.04, 390.07, 390.12, 391, 392, 253

[56] References Cited

U.S. PATENT DOCUMENTS

| | | | |
|---|---|---|---|
| Re. 27,579 | 2/1973 | Youmans | 376/159 |
| 2,395,322 | 2/1946 | Evans | 97/47 |
| 2,557,158 | 6/1951 | Teichmann | 250/83.6 |
| 2,562,914 | 8/1951 | Herzog | 250/83.6 |
| 2,781,453 | 2/1957 | Belcher et al. | 250/83.6 |
| 2,800,847 | 7/1957 | Bennett | 97/46.39 |
| 3,008,046 | 11/1961 | Carpenter | 250/71.5 |
| 3,124,684 | 3/1964 | Eberline | 250/71.5 |
| 3,256,438 | 6/1966 | Armistead | 376/159 |
| 3,341,706 | 9/1967 | Swift et al. | 250/83.3 |
| 3,354,310 | 11/1967 | Swift | 250/83.3 |
| 3,433,310 | 3/1969 | Harper | 172/471 |
| 3,444,721 | 5/1969 | Hearn et al. | 73/23 |
| 3,463,922 | 8/1969 | Senftle et al. | 376/159 |
| 3,715,758 | 2/1973 | Sender | 343/112 R |

(List continued on next page.)

FOREIGN PATENT DOCUMENTS

0081075  6/1983  European Pat. Off. .

OTHER PUBLICATIONS

B. D. Sowerby, "On–Line and Bulk Analysis of Coal . . . ," Journal of Radioanalytical and Nuclear Chemistry, Articles, vol. 123, Feb. 8, 1988, pp. 61–75.

H. R. Meyer et al., "Field Instruments Developed For Radiation Measurements of the UMTRA Project," Pub. in Proceedings, Waste Management, Mar. 1987, U. of Arizona.

G. M. Worth et al., "Use of Commercial Ranging System in Field Surveys of Radioactively Contaminated Sites," 1984 IEEE Nuclear Science Symposium, Oct. 31 to Nov. 2, 1984.

(List continued on next page.)

*Primary Examiner*—Harvey E. Behrend

[57] ABSTRACT

A system for determining depth profiles of concentrations of hazardous elements in soils comprises a neutron source for generating neutrons of a first energy level and irradiating a volume of soil with the neutrons. Nuclear reactions are effected within the soil and gamma radiation is emitted from the soil. The system also includes an array of gamma detectors for detecting gamma radiation emitted from the soil; source electronics for controlling the width of regularly repeated pulses of neutrons generated by the neutron source; detector electronics associated with the gamma detectors for amplifying and digitalizing signals generated by the gamma detectors and storing data representing the digitalized signals; spectral analysis software for analyzing the data and determining the concentrations of selected target elements in the soil; and an acquisition interface module (AIM). The AIM controls the timing of the source and detector electronics such that the neutron source generates neutrons in regularly repeated bursts of a prescribed pulse width and the detectors and detector electronics detect gamma rays during a plurality of time intervals associated with the burst and acquire groups of data. Each group is indicative of a number of gamma rays emitted and their energy levels during a corresponding time interval. The system also includes a mobile platform carrying the neutron source, array of gamma ray detectors and software for determining a depth profile of a target element. Trace elements can also be detected with the disclosed system.

12 Claims, 8 Drawing Sheets

U.S. PATENT DOCUMENTS

| | | | |
|---|---|---|---|
| 3,723,727 | 3/1973 | Wogman et al. | 250/83.3 |
| 3,781,556 | 12/1973 | Taylor et al. | |
| 3,801,816 | 4/1974 | Arnold | 250/270 |
| 3,825,751 | 7/1974 | Johnson, Jr. et al. | 250/253 |
| 3,832,545 | 8/1974 | Barkto | 250/312 |
| 3,889,112 | 6/1975 | Holmes et al. | 376/159 |
| 3,918,056 | 11/1975 | Merrick | 343/6.5 LC |
| 3,938,146 | 2/1976 | Dano | 343/6.5 LC |
| 4,056,969 | 11/1977 | Barringer | 73/28 |
| 4,232,220 | 11/1980 | Hertzog | 250/270 |
| 4,232,317 | 11/1980 | Freeny, Jr. | 343/112 |
| 4,248,310 | 2/1981 | McWilliams | 172/661 |
| 4,278,885 | 7/1981 | von Alfthan et al. | 250/370 |
| 4,302,285 | 11/1981 | Pronman et al. | 376/159 |
| 4,314,155 | 2/1982 | Sowerby | 250/253 |
| 4,317,033 | 2/1982 | Panenka et al. | 250/253 |
| 4,350,887 | 9/1982 | Barnard et al. | 250/265 |
| 4,421,981 | 12/1983 | Hough | 250/253 |
| 4,464,330 | 8/1984 | Speir et al. | 376/159 |
| 4,483,817 | 11/1984 | Evans et al. | 376/159 |
| 4,581,531 | 4/1986 | Dion | 250/253 |
| 4,645,926 | 2/1987 | Randall | 250/270 |
| 4,754,136 | 6/1988 | Blakely | 250/301 |
| 5,025,150 | 6/1991 | Oldham et al. | 250/253 |
| 5,038,042 | 8/1991 | Hansen et al. | 250/368 |
| 5,068,532 | 11/1991 | Wormald | 250/270 |
| 5,133,901 | 7/1992 | Peterson | 252/626 |
| 5,162,095 | 11/1992 | Alegre et al. | 376/159 |

OTHER PUBLICATIONS

D. H. Jensen et al., "Status of a Pulsed–Neutron Logging Probe Using a High–Purity Germanium Detector," IEEE Transactions on Nuclear Science, vol. NS–30, No. 2, Apr. 1983, pp. 1657–1663.

L. Evans, "In Situ Elemental analysis Using Nutron–Capture Gamma–Ray Spectroscopy," Nuclear Instruments and Methods, (North–Holland, 1982), pp. 353–357.

L. Evans, "Determination of Elemental Composition in Geochemical Exploration Using A 14–MeV Neutron Generator" IEEE Transactionson Nuclear Science, I. Experimental Aspects, vol. NS–28, No. 2, Apr. 1981 pp. 1626–1628.

J. Lapides, "Determination of Elemental Composition in Geochemical Exploration Using A 14–MeV Neutron Generator" II. Theoretical Aspects, IEEE Transactions on Nuclear Science, vol. NS–28, No. 2, Apr. 1981, pp. 1629–1631.

J. McKlveen, "A Compilation of Fast Neutron Interactions, Cross Sections, Gamma Spectra and Gamma Decay Energies" IEEE Transactions on Nuclear Science, vol. NS–28, No. 2, Apr. 1981, pp. 1632–1634.

C. Herzenberg, "Use of Small Accelerators in Coal Analysis and Coal Slurry Flow Measurements," IEEE Transactions on Nuclear Science, vol. NS–26, No. 1 Part 2 of 2 Parts, Feb. 1979, pp. 1568–1573.

Neutron Sources and Publications, Proceedings of the American Nuclear Society National Topical Meeting, Sptil 29–32, 1971, Conf. 710402, vol. III, "A Prompt Gamma––Ray Coal Analysis, System," IV–40 to IV–46.

L. Evans, "Inter–Pulse High–Resolution Gamma–Ray Spectra Using A 14 MeV Pulsed Neutron Generator," Nuclear Instruments and Methods in Physics Research 219 (1984) pp. 233–242.

W. E. Clem, "Mobile Surface Contamination Monitor for Large Area Radiological Surveillance," pp. 1–4.

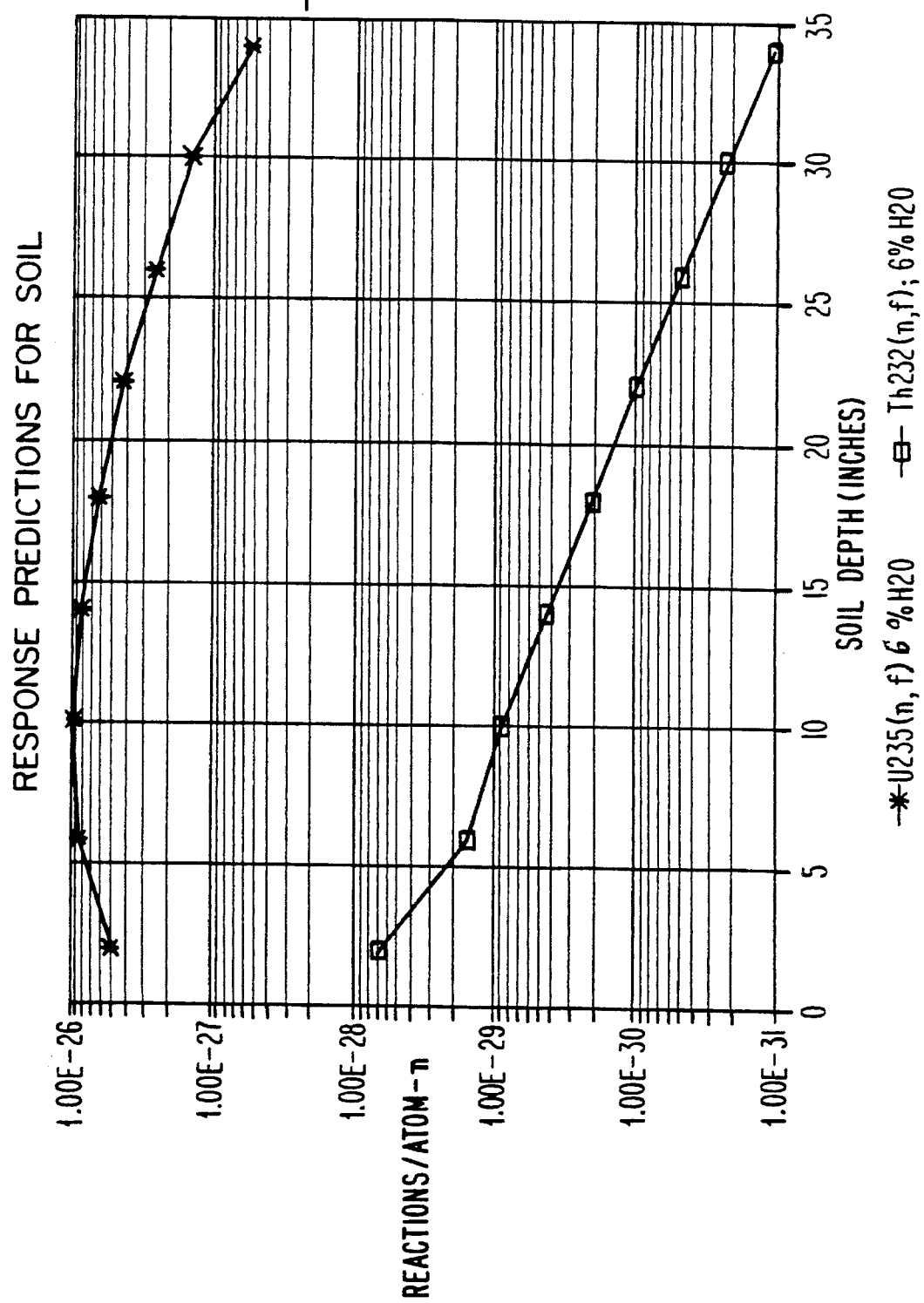

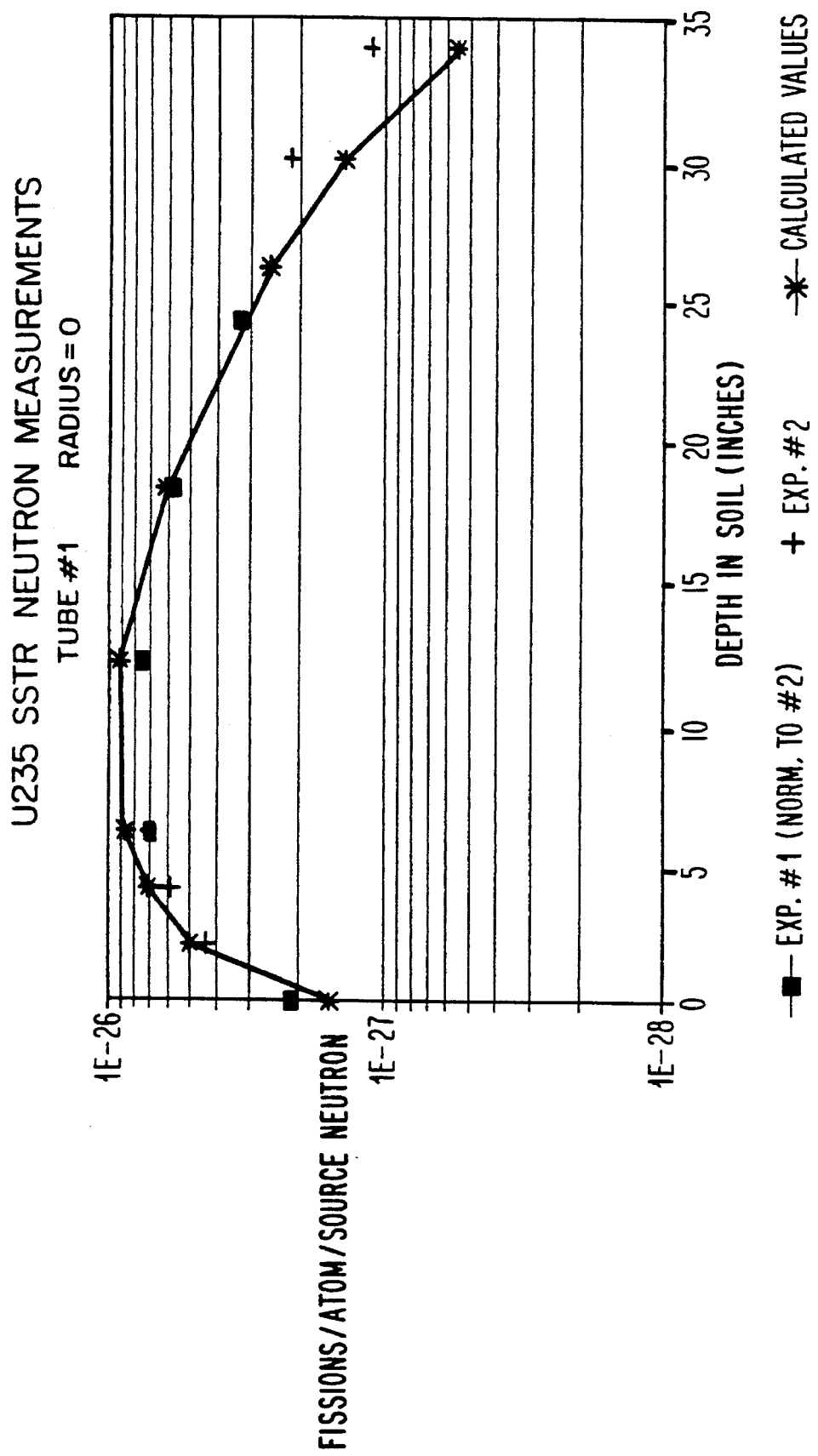

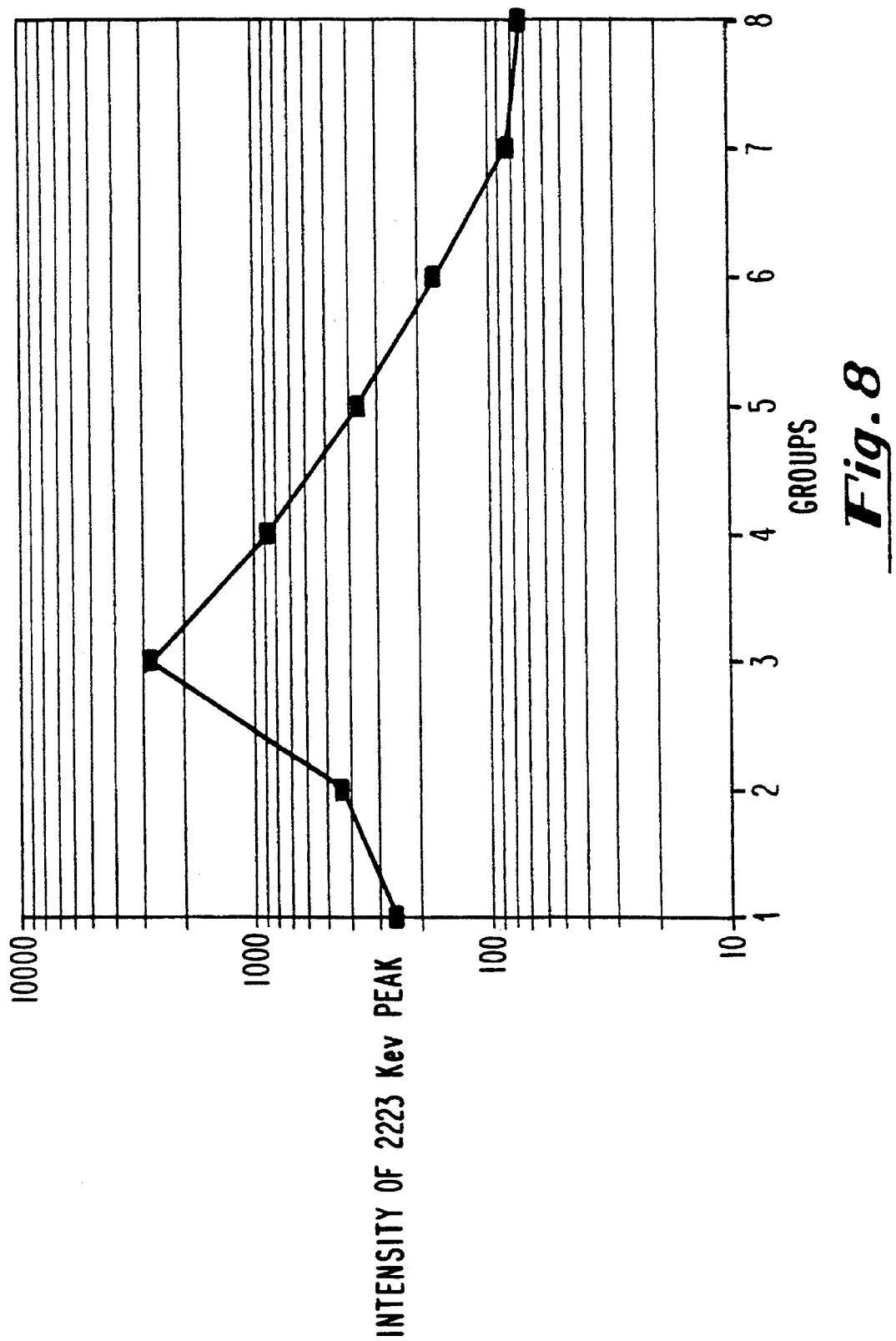

PROMPT GAMMA NEUTRON ACTIVATION ANALYSIS SYSTEM

BACKGROUND OF THE INVENTION

The present invention generally relates to PGNAA (prompt gamma neutron activation analysis), and more particularly relates to methods and apparatus that apply PGNAA to soil remediation.

With the growing awareness of the contamination of large tracts of land with chemically or radioactively hazardous elements, there is a corresponding international effort to initiate remediation activities to restore affected regions to an environmental status considered acceptable. To this end, soil washing and other methods are being developed. For these methods to be technically efficient and cost effective, it is necessary to accurately identify where the contamination in a field is located. In addition, it is necessary to have, to the greatest extent possible, inline monitoring of remediation process streams, to determine when the treated soil is acceptable for release back to the field. The latter need has been met by a system described in U.S. Pat. No. 5,133,901, Jul. 28, 1992, titled *System and Method for On-line Monitoring and Control of Heavy Metal Contamination in Soil Washing Process*, which is hereby incorporated by reference into this specification.

Neutron-induced reactions can be divided into two broad categories, threshold reactions and exoergic reactions. For threshold reactions, energy in the form of neutron kinetic energy is required to supply a certain minimum energy to the reaction system before the reaction can proceed. Neutrons with energies below this minimum threshold energy are incapable of inducing the nuclear reaction. For exoergic reactions, the threshold is zero; that is, neutrons with all energies are capable of inducing the reaction. Since neutrons lose energy via nuclear collisions, the minimum energy possible for a neutron is determined by the thermal motion of the atoms in the stopping medium. Neutrons with this minimum average energy are referred to as thermal neutrons and have a mean energy of approximately 0.0252 eV.

FIG. 1 illustrates the process of neutron activation at a nuclear level. A neutron of energy E collides with the nucleus of an atom in the sample and initiates a reaction. For a neutron of thermal energy, the reaction might be absorption of the neutron into the nucleus, creating the next higher mass isotope of that element. If the neutron is more energetic (e.g., with several mega-electronvolts of kinetic energy), other nuclear reactions are possible. These other reactions include inelastic scattering from the nucleus, exciting the atom according to its internal structure of quantum levels, or other reactions ((n,p), (n, alpha), (n,2n), etc.) in which nuclear transmutation to another element occurs. In each of these cases, the residual nucleus is left in a highly excited internal state, and decays to its ground state almost instantaneously ($10^{-14}$ seconds or less), emitting a gamma ray of several mega-electronvolts of energy. The energy of this gamma ray is uniquely characteristic of the quantum structure of the residual nucleus, and thus is a signature of the original target nucleus. The number of atoms of each of the elements of interest in a sample can be estimated by detecting and collecting the spectrum of gamma rays emitted by the sample and integrating the appropriate peaks.

The PGNAA process is governed by the following equation:

$$A = N\sigma\phi B,$$

where:

A=disintegrations per second producing the desired gamma rays,

N=the number of target nuclei for the reaction, $\sigma$=the reaction cross section ($10^{-24} \text{cm}^2$), $\phi$=the flux of neutrons of the required energy ($\text{cm}^{-2}\text{-sec}^{-1}$), B=the branching ratio, i.e., a fraction between 0 and 1 indicating how often this capture produces the gamma ray of interest.

SUMMARY OF THE INVENTION

In light of the growing need for soil remediation, a primary object of the present invention is to provide methods and apparatus for accurately characterizing soil fields. A further object of the present invention is to provide PGNAA methods and apparatus for providing a depth profile of the contaminants in a soil field. Another object of the present invention is to provide PGNAA methods and apparatus for detecting trace elements in a soil field.

A method for analyzing an interrogation volume in accordance with the present invention comprises the steps of irradiating an interrogation volume with a neutron burst characterized by an intensity and pulse width, and thereby effecting an emission of gamma radiation from the interrogation volume; acquiring groups of gamma radiation data during a plurality of time intervals, each group being indicative of the number or intensity of gamma rays and energy of the gamma rays during a corresponding time interval, and a first group corresponding to a first interval during which the neutron burst is on; and analyzing the gamma data to detect the presence and determine the amount of a prescribed target element in the interrogation volume.

In one preferred embodiment of the invention, the pulse width is approximately 100–200 µs and the plurality of time intervals spans approximately 5000 µs.

In addition, in one embodiment described herein the method includes generating neutrons with energies of approximately 14 MeV, 3 MeV, and 0.025 eV. While these energies are conveniently available, other energies are also available and useful for various applications, e.g., 750 keV neutrons can be produced using a proton linear accelerator and a lithium target.

The method may also advantageously include the step of analyzing the gamma data to determine whether the prescribed target element is present within a first prescribed depth range in the interrogation volume. Further, the method may include the step of generating depth profile data representing the amount of the target element at a plurality of depth ranges in the interrogation volume.

In one example of the invention, the analyzing step for determining whether the target element is present within a first prescribed depth range comprises the step of computing a depth at which the neutrons have energy appropriate to initiate a reaction that produces gamma radiation indicative of the target element.

In a second example of the invention, the method further comprises the following steps:

determining calibration data by carrying out the following sub-steps:

(1) placing a slug of mass M of the target element at a plurality of depths, including: 0 inches; $X_1$, where $X_1$ is the deepest depth from which gamma rays of energy $E_1$ can escape the interrogation volume in sufficient numbers to be detected; and $X_2$, where $X_2$ is the deepest depth from which gamma rays of energy $E_2$ can escape the interrogation volume in sufficient numbers to be detected; and measuring yields $Y_{E1}(0)$, $Y_{E1}(X_1)$ of gamma rays of energy $E_1$ at depths of 0 inches and $X_1$, respectively, and $Y_{E2}(0)$, $Y_{E2}(X_1)$, $Y_{E2}(X_2)$ of gamma rays of energy $E_2$ at depths of 0 inches, $X_1$ and $X_2$, respectively;

(2) defining the following ratios:

$$R_{21}(0) = \frac{Y_{E2}(0)}{Y_{E1}(0)}$$

$$R_{21}(X_1) = \frac{Y_{E2}(X_1)}{Y_{E1}(X_1)}$$

performing a field measurement of yields $y(E_1)$, $Y(E_2)$ of gamma rays of energies $E_1$, $E_2$, respectively;

performing a depth inference calculation by determining whether $y(E_2)/y(E_1)$ is greater than $R_{21}(X_1)$ and whether $y(E_1)$ is greater than 0, and then determining a range of depths at which the target element is located by the following formulas:

Case 1 if $y(E_2)/y(E_1)$ is greater than $R_{21}(X_1)$ and $y(E_1)$ is greater than 0, then the target element is present between 0 and $X_1$ and between $X_1$ and $X_2$;

Case 2 if $y(E_2)/y(E_1)$ is less than $R_{21}(X_1)$ and $y(E_1)$ is greater than 0, then the target element is between 0 and $X_1$;

Case 3 if $y(E_2)$ is greater than 0 and $y(E_1)$ is 0, then the target element is between $X_1$ and $X_2$; and then, performing an equivalent mass calculation by the following formulas:

Case 1

$$ES_{max}(0 - X_1) = \frac{y(E_1)}{Y_{E1}(X_1)} M$$

$$ES_{min}(0 - X_1) = \frac{y(E_1)}{Y_{E1}(0)} M$$

$$ES_{max}(X_1 - X_2) = \frac{y(E_2) - y(E_1)R_{21}(0)}{Y_{E2}(X_2)} M$$

$$ES_{min}(X_1 - X_2) = \frac{y(E_2) - y(E_1)R_{21}(X_1)}{Y_{E2}(X_1)} M$$

Case 2

$$ES_{max}(0 - X_1) = \frac{y(E_2)}{Y_{E2}(X_1)} M$$

$$ES_{min}(0 - X_1) = \frac{y(E_2)}{Y_{E2}(0)} M$$

or, $$ES_{max}(0 - X_1) = \frac{y(E_2)}{Y_{E2}(X_1)} M$$

$$ES_{min}(0 - X_1) = \frac{y(E_2)}{Y_{E2}(0)} M$$

Case 3

$$ES_{max}(X_1 - X_2) = \frac{y(E_2)}{Y_{E2}(X_2)} M$$

$$ES_{min}(X_1 - X_2) = \frac{y(E_2)}{Y_{E2}(X_1)} M$$

($ES_{max}$ and $ES_{min}$ represent the maximum and minimum equivalent mass within the specified ranges.)

The present invention also encompasses systems (hardware) for carrying out the steps described above. For example, the present invention encompasses mobile systems for determining depth profiles of concentrations of hazardous elements in soils. Such a system in accordance with the invention comprises a neutron source for generating neutrons of a first energy level and irradiating a volume of soil with the neutrons, whereby nuclear reactions are effected within the soil and gamma radiation is emitted from the soil; an array of gamma detectors for detecting gamma radiation emitted from the soil; source electronics means associated with the neutron source for controlling a pulse width of neutrons generated by the neutron source, the pulse width defining an interval of time during which neutrons are emitted from the neutron source; detector electronics means associated with the gamma detectors for amplifying and digitalizing signals generated by the gamma detectors and storing data representing the digitalized signals; spectral analysis means for analyzing the data and determining concentrations of selected target elements in the soil; and an acquisition interface module (AIM) for controlling the timing of the source and detector electronics such that the neutron source generates neutrons in a burst of a prescribed pulse width and the detectors and detector electronics means detect gamma rays during a plurality of time intervals associated with the burst and acquire groups of data, each group being indicative of a number of gamma rays emitted and their energy levels during a corresponding time interval, and a first group corresponding to a first interval during which neutrons are being generated by the source. A preferred embodiment further comprises a mobile platform. In this embodiment, the array of gamma ray detectors comprises a plurality of gamma ray detectors mounted on the mobile platform. This embodiment also comprises means for determining a depth profile of a target element.

In addition, the present invention encompasses a high sensitivity PGNAA method for detecting particular signature gamma rays generated by neutron-induced reactions within a sample interrogation volume. The reactions include threshold or fast neutron-induced reactions, which occur instantaneously; thermal neutron-induced reactions, which require time for the neutrons to be moderated to thermal energies; and radionuclide production. The method comprises the following steps: (1) irradiating the sample with a pulsed neutron source; and (2) if the gamma rays of interest are generated by a threshold or fast neutron-induced reaction, counting gamma rays emitted from the sample only during the neutron pulse on-times, thereby enhancing detection of fast neutron-induced gamma rays relative to thermal neutron-induced gamma rays, radionuclide gamma rays, and background gamma rays; or (3) if the gamma rays of interest are generated by a thermal neutron-induced reaction, counting gamma rays emitted from the sample immediately following the neutron pulse on-times and for a duration of hundreds of micro-seconds thereafter.

Other embodiments of the invention also include a step of or means for improving gamma signal-to-noise ratio using Compton suppression.

Other features of the present invention are described below.

BRIEF DESCRIPTION OF THE DRAWINGS

FIG. 5 is a graph of predicted number of reactions per atom per neutron versus depth.

FIG. 6 is a graph of experimentally measured and predicted fission responses for $^{235}U$ versus depth.

FIG. 8 is a graph of the intensity of the 2223 keV peaks of groups 1–8 (G1–G8) of FIG. 7.

DETAILED DESCRIPTION OF PREFERRED EMBODIMENTS

The system described herein employs PGNAA to determine the concentration and depth profile of hazardous elements in a field of soil. One embodiment employs a neutron generator tube in three configurations as a source of 14 MeV neutrons, 3 MeV neutrons, or thermal (~0.025 eV) neutrons at the soil surface. As the neutrons penetrate the soil, they activate the contents by both thermal capture and fast neutron induced reactions. The concentration of selected elements is determined by detecting the resulting instantaneously emitted (prompt) gamma rays, which are characterized by high and distinct energies indicative of the activated elements. A depth distribution of the concentration of hazardous elements beneath the soil surface is derived through a knowledge of the depth at which the neutron field had the energy (thermal or some threshold) required to initiate the reaction. Two methods for deriving a depth profile of contaminants are described below.

One embodiment of the present invention is a mobile system for acquiring depth profiles of concentrations of hazardous materials in soil. Another embodiment of the present invention is a high sensitivity PGNAA system for detecting trace elements. These embodiments are described below.

I. MOBILE SYSTEM FOR ACQUIRING DEPTH PROFILES OF CONCENTRATIONS OF HAZARDOUS MATERIALS IN SOIL

Figure 2A:
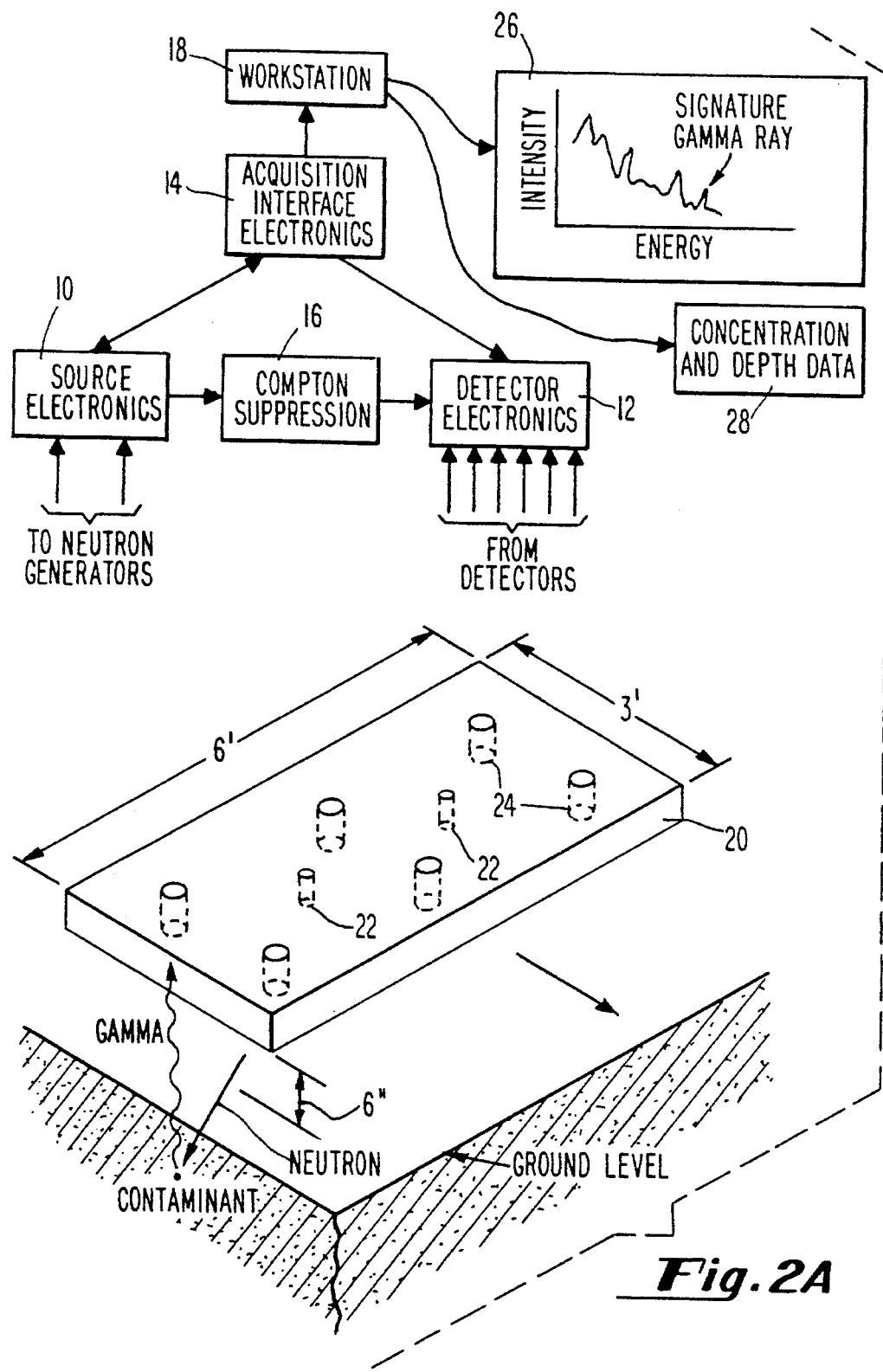
FIG. 2A is a schematic diagram of one embodiment of a PGNAA system in accordance with the present invention.
Figure 2B:
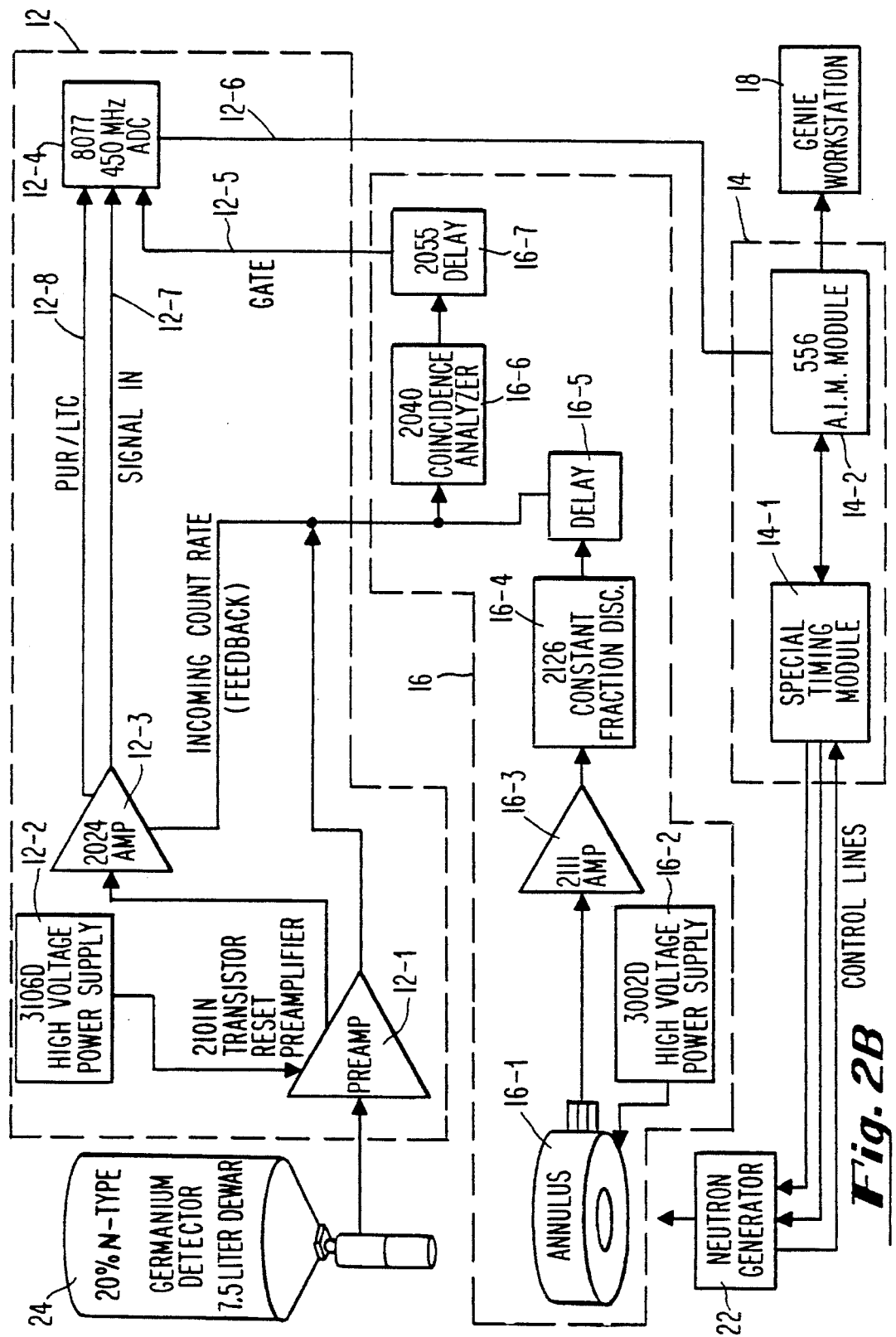
FIG. 2B is a more detailed schematic diagram of the electronics of the system depicted in FIG. 2A.

FIGS. 2A and 2B depict one embodiment of a mobile PGNAA field survey unit in accordance with the present invention.

Referring to FIG. 2A, an exemplary embodiment of a mobile PGNAA field survey unit in accordance with the present invention comprises a source electronics block 10; a detector electronics block 12; an acquisition interface electronics block 14; a Compton Suppression block 16; a computer work station 18; a mobile or movable platform 20; a pair of neutron sources 22 carried by the platform 20 and capable of producing approximately $10^7$ thermal neutrons per $cm^2$ per second in a layer from 3 inches to 9 inches below the surface; six gamma ray detectors 24 carried by the platform 20; a display 26 for displaying measured gamma ray spectra; and memory 28 for memorizing calculated concentration and depth data. In the embodiment depicted in FIG. 2A, the mobile platform 20 is approximately 6 feet long by 3 feet wide and is carried approximately 6 inches above ground level. These dimensions are only examples. In addition, the mobile vehicle itself is not considered part of the present invention and therefore is not depicted or described in detail in this specification. Further, the interconnections between the source electronics and the neutron sources and the neutron detectors have been omitted from FIG. 2A to make the drawing more legible. Further details of the system of FIG. 2A are shown in FIG. 2B.

Referring now to FIG. 2B, one embodiment of the invention includes the following specific components:

Pulse Processing Electronics 12

High-speed, high throughput count rate preamplifier 12-1. For example, a Canberra Model 2101N Transistor Reset Preamplifier.

Detector High Voltage Supply 12-2 capable of 0–3000 volts. For example, a Canberra Model 3106D High Voltage Power Supply.

High count rate, high speed spectroscopy amplifier 12-3. For example, a Canberra Model 2024 Spectroscopy Amplifier.

High Speed ADC 12-4 (either multiple approximation or high frequency (at least 400 MHz) Wilkinson-type ADC). For example, a Canberra Model 8077 ADC. (A gate signal line 12-5, AIM module input 12-6, ADC input 12-7, and PUR/LTC (Pileup Correction/Live Time Correction) input 12-8 are also depicted.)

Acquisition Interface Electronics 14

Special Timing Module 14-1 to coordinate firing of neutron generator with gamma pulse acquisition.

Acquisition Interface Module 14-2, e.g., Canberra Model 556.

Compton Suppression Detector and Associated Electronics 16

23 cm diameter×23 cm high NaI(Tl) crystal with an 8 cm diameter annulus and associated photomultiplier tubes (see 16-1). For example, a Solon Technologies Special MBW Assembly.

High voltage power supply 16-2, e.g., a Canberra Model 3002D High Voltage Power Supply.

High speed amplifier 16-3, e.g., a Canberra Model 2111 Amplifier.

Constant Fraction Discriminator 16-4, e.g., Canberra Model 2126.

Gate Pulse Delay Unit 16-5, e.g., Canberra Model 2055.

Coincidence Analyzer 16-6, e.g., Canberra Model 2040.

Multi-Channel Analyzer and High-speed Minicomputer (block 18)

For example, Canberra VAX/VMS Genie Workstation.

Neutron Generator 22

Pulsed D-T or D-D electronic neutron generator with variable pulse widths in the 100–750 μs range and capable of delivering 50–1000 pulses per second. For example, a specially modified MF Physics A-320 neutron generator.

Gamma Detector 24

20% N-type neutron resistant high purity germanium (HPGe) detector. For example, a Canberra Model GR2019 HPGe Detector.

7.5 liter $LN_2$ Dewar, e.g., a Canberra 7906-7.5SL vertical integral cryostat.

The development of the system depicted in FIGS. 2A and 2B involved determining an acceptable configuration of neutron sources and gamma ray detectors, and determining the calibration of peak intensity to elemental concentration for each element to be detected. The system components were selected according to the elements to be detected and the reactions to be used in detecting them. For example, activation through thermal neutron capture is useful for detecting uranium, thorium, cadmium, copper and many other elements.

To achieve a depth profile of an element detectable by thermal neutron activation, one should use several sources which produce significant thermal neutron fluxes at very different average depths in the soil. To this end, the system of FIGS. 2A, 2B scans the ground using several different types of source, including:

1) a DT neutron generator tube, which accelerates deuterons into tritium to make d+t fusion, producing neutrons of energy approximately 14 MeV; this produces a significant thermal neutron flux at approximately 1 to 2 feet below the soil surface;

2) a DD neutron generator tube, which uses d+d fusion to produce neutrons of energy approximately 3 MeV; this produces a significant thermal neutron flux several inches below the soil surface;

3) a DD or DT neutron generator tube, surrounded above ground by a large quantity of hydrogenous material, which has the effect of creating a large thermal neutron flux at the soil surface;

4) other systems (e.g., the proton linear accelerator approach) capable of providing a controllable, regular pattern of neutron bursts.

In the DT tube case, there will be a significant neutron flux at energies (several MeV and higher) above the respective thresholds for inducing fast neutron reactions. Although fast neutron reactions are characterized by cross sections considerably smaller than thermal neutron reaction cross sections, fast neutron reactions also produce prompt signature gamma rays of high energy and thus can add information about the depth profile of particular elements. This is discussed further below.

To estimate the performance of the system depicted in FIGS. 2A, 2B, a case (achievable with the DT or moderated DT configuration mentioned above) where there is a region of thermal flux of approximately $10^7$ n/cm$^2$-sec in a volume beginning 3 inches (7.6 cm) below the surface and extending to 9 inches (22.9 cm) below the surface was considered. This is achievable by using two or three neutron tubes each generating between $10^9$ and $10^{11}$ neutrons per second. (It should be noted that, in many applications, lower neutron fluxes will provide adequate system performance, as indicated by laboratory measurements. This alleviates the level of throughput-related complexity that could be associated with a very high thermal flux.) Table 1 is based on the 6 ft. by 3 ft. (1.89 m×0.91 m), six detector embodiment depicted in FIG. 2A; it lists the total number of counts (gamma rays) per second expected to be intercepted by the set of 6 detectors for the elements listed. In estimating the count rates listed in Table 1, a specific group of activation gamma rays was assumed detected for each element. The assumed concentrations of elements in the soil are consistent with guidelines for clean soil currently recognized by regulatory agencies. In addition, by assuming that, on average, background counts are four times the true signal, the respective measurement times required for a standard deviation of 25% in the inferred concentrations of the given elements has been estimated. This corresponds to 144 true counts recorded during the measurement interval. Further, it has been assumed that Pb will be detected through the use of fast neutron induced gamma rays from inelastic scattering.

TABLE 1

| Element | ppm in soil by mass | Expected counts/sec | Counting time (sec) |
|---------|--------------------|--------------------|--------------------|
| Cl | 300 | 86.4 | 2 |
| Cu | 250 | 4 | 36 |
| Cd | 10 | 5.1 | 29 |
| Fe | 300 | 5.3 | 28 |
| Hg | 2 | 2 | 72 |
| Ni | 300 | 7.2 | 20 |
| Pb | 50 | 0.9 | 160 |
| Th | 105 | 3.3 | 44 |
| U | 42 | 0.8 | 180 |

Table 1 indicates that the present invention provides a substantial amount of data in minutes of interrogation time, even considering only the thermal neutron activation component of the available data. Thus, with an online computer analysis system, an entire 50 ft. by 50 ft. (15.2 m×15.2 m) area can be evaluated at a single depth in approximately ten hours. A three region depth profile can be acquired in approximately thirty hours. These performance estimates are for the 6 ft. by 3 ft., six detector embodiment of FIG. 2A. A larger area of coverage per interrogation could be achieved simply by increasing the dimensions, number of detectors, and number of sources. In addition, it should be noted that, although the above data was generated for a few elements of interest, the present invention may be employed to detect concentrations of elements across the periodic table.

Both fast neutron induced reactions and thermal neutron induced reactions are mentioned above but, in the estimate of performance, only thermal neutron capture is considered, except in the case of Pb, for which inelastic scattering was assumed. As discussed above, even in nuclides with low thermal capture cross sections (e.g., $^{12}$C or the Pb isotopes), inelastic scattering of a neutron will produce a prompt signature gamma ray and thus provide an alternate method of element identification. In many nuclides, threshold reactions such as (n,p) or (n,$\alpha$), which often require a minimum incident neutron energy before the reaction can proceed, are also likely. Each of these reactions produces its own set of unique, signature prompt gamma rays. Therefore, extension of the neutron field to contain fast, thermal and intermediate energy components will extend the versatility of the system by extending the variety of reaction channels that can be used for element identification.

Moreover, since depth profiles of the various energy components of the neutron field can be reliably calculated with several well-validated transport codes (e.g., DOT or MCNP), the response of signature gamma rays from reaction channels initiated by neutrons of differing energy regimes can also be used to infer contamination depth profiles. This is discussed further below.

To generate neutrons of energies sufficient to initiate most fast neutron induced reactions, the most commonly used sources are electronic neutron generator tubes of the type developed for oil well logging applications. These tubes contain a compact accelerator which propels deuterons into tritium or deuterium at an incident kinetic energy of 100–200 keV. This produces fusion reactions, with a resulting neutron yield. The D+T reactions produce 14 MeV neutrons and the D+D reactions produce 2–3 MeV neutrons.

II. TIMING OF NEUTRON PULSES AND GAMMA ACQUISITION

Whether using a Cf (Californium) source or an electronic neutron generator, there is a tendency for the signal processing circuitry to experience saturation effects due to the high rate of prompt gamma ray production while the neutrons are being emitted. This can lead to a severe reduction of gamma energy data throughput, to the point of rendering the acquisition system completely inactive in extreme cases. This situation can be remedied in two ways: (1) by employing fast electronics, including, e.g., transistor reset preamplifiers and fast spectroscopy amplifiers having the best possible signal handling capability; and (2) by modifying the timing of the neutron emissions from the tube such that the rate of emissions will be matched to the circuit signal processing capability.

Most neutron generator tubes produce a very intense burst of neutrons within the first few microseconds of each pulse period. A typical pulse duration is 8 µs. This timing is not within the user's control in most systems. By allowing the neutron on-time (pulse width) and period to be adjustable, the same average number of neutrons can be produced per unit time using a longer on-time per pulse period. This enables one to reduce the instantaneous load on the signal processing system during the neutron on-time to a level the detector electronics can handle without severe degradation of data throughput. With the present invention, the prompt gamma rays produced by fast neutrons are detectable at levels sufficient for element identification instead of being lost because of saturation effects in the electronics.

There are two reasons why it is advantageous to separate acquisition of prompt gamma rays produced by fast neutrons and prompt gamma rays produced by thermalized neutrons: First, having a separation of fast neutron induced gamma rays and thermal neutron induced gamma rays simplifies spectral interpretation. Second, this optimizes the signal-to-background ratio for the thermal neutron induced prompt gamma rays by minimizing the data representing long-lived activity.

Such timing control requires three major system components:

1. A neutron generator with adjustable pulse period and neutron on-time, or duty cycle.
2. Fast electronics in preamplifiers, spectroscopy amplifiers and other signal processing components.
3. An electronic control system that can control the neutron pulse characteristics and also acquire and store the data in separate "fast neutron prompt gamma," "thermal neutron prompt gamma" and "long lived activity" buffers.

The system must acquire gamma ray spectral data in distinct time slices: one or more representing the on-time of the neutrons (intentionally kept small compared to the expected time—typically several hundred microseconds—for neutrons to thermalize (slow down) in the irradiated medium) and one or more encompassing some or all of the remaining time between neutron bursts. Such a scheme allows one to empirically identify the separate time regimes appropriate to the fast neutron prompt gamma rays, thermal neutron prompt gamma rays, and long lived activity, without including unnecessary gamma data in the respective buffers.

Figure 1:
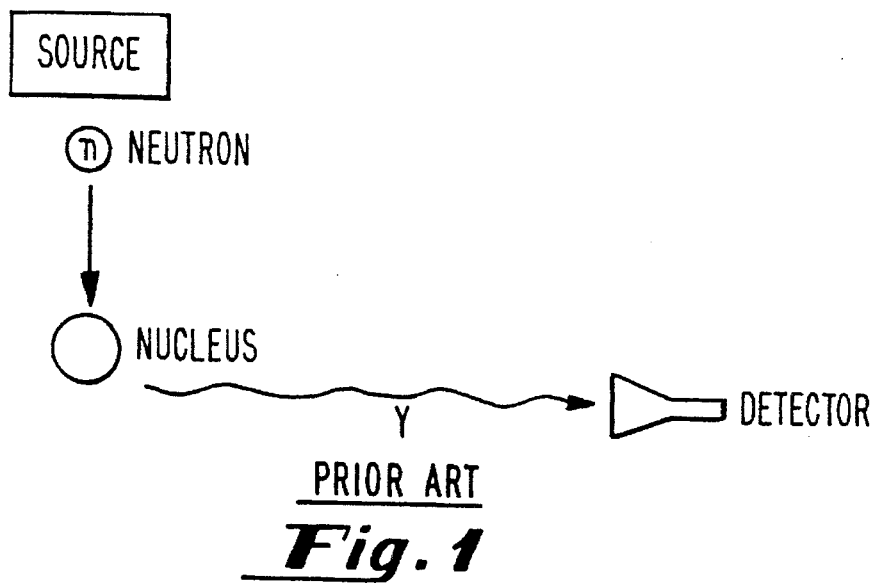
FIG. 1 is a schematic diagram of a basic PGNAA system.
Figure 3:
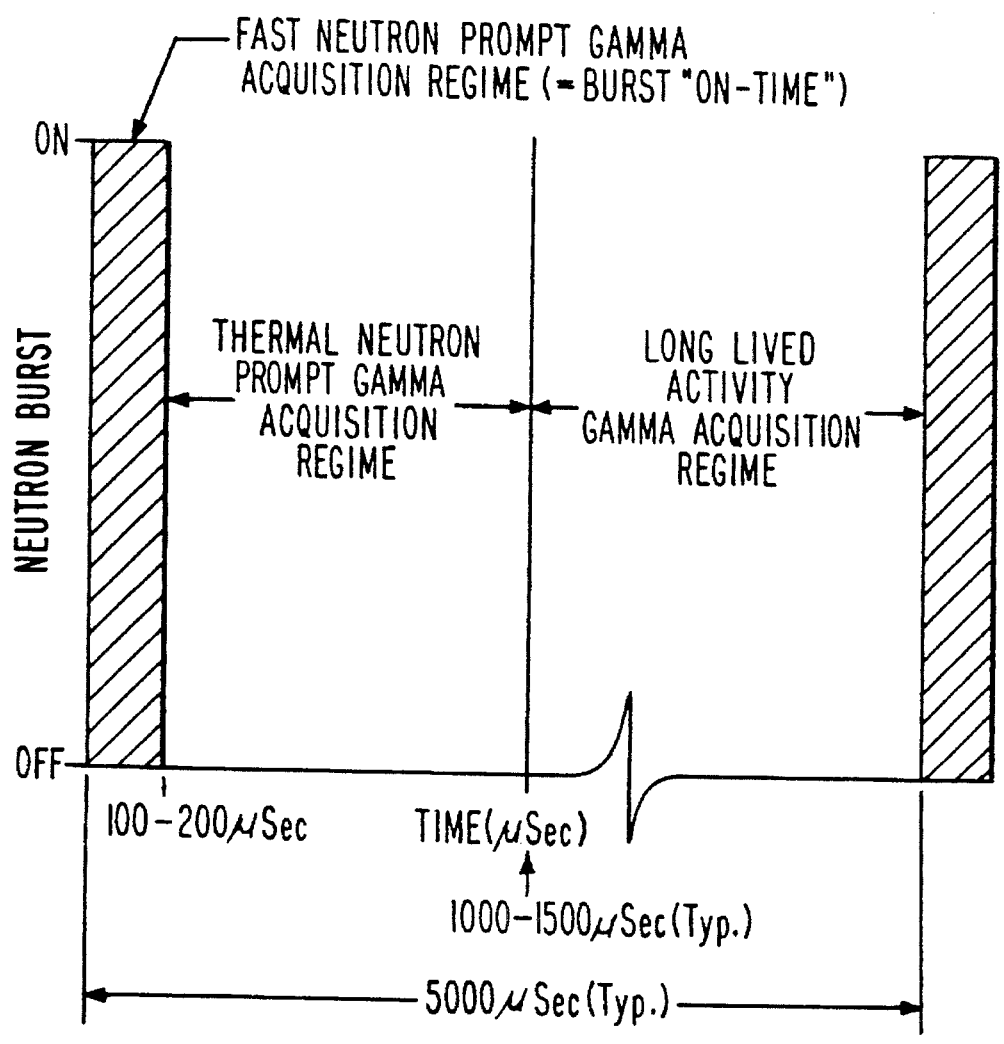
FIG. 3 is a timing diagram for a PGNAA system in accordance with the present invention.

This approach is illustrated in FIG. 3, which illustrates the timing of the gamma ray acquisition protocol. As shown, the neutron burst pulse width is approximately 100 to 200 microseconds and the pulse repetition period is approximately 5000 microseconds. The neutron burst on-times are represented by the shaded regions in FIG. 3. During the burst on-time, gamma rays produced by fast neutrons are detected; thereafter, in an interval encompassing approximately 1000 to 1500 microseconds starting at the end of the neutron burst on-time, gamma rays produced by thermal neutron activation are detected; then, after this second acquisition regime, gamma rays produced by long-lived neutrons are detected.

One embodiment of a pulsed PGNAA system in accordance with the present invention includes the above-described neutron generator tube and detection and control electronics. The pulsed PGNAA system can advantageously be employed in the mobile field survey application described above.

Figure 4A:
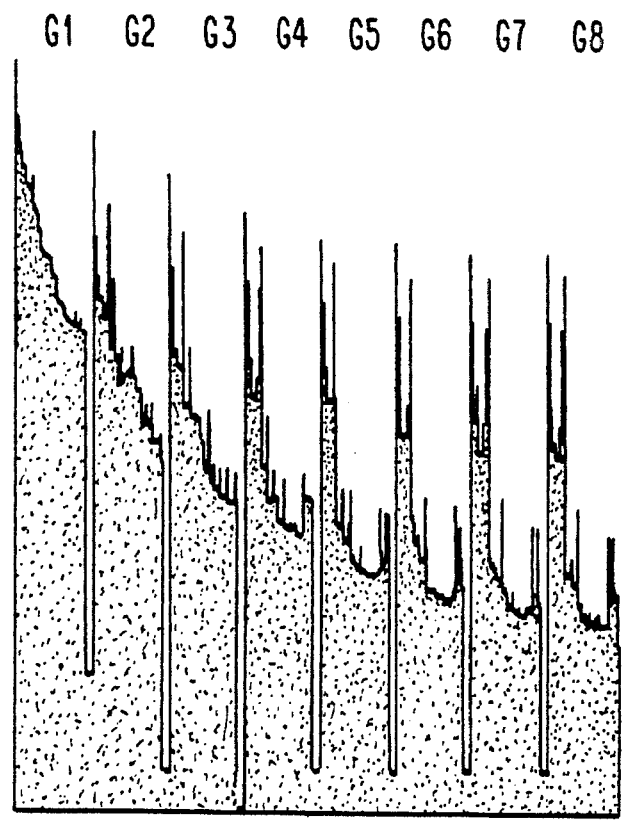
FIGS. 4A and 4B depict exemplary gamma ray spectra obtained in accordance with the present invention.
Figure 4B:
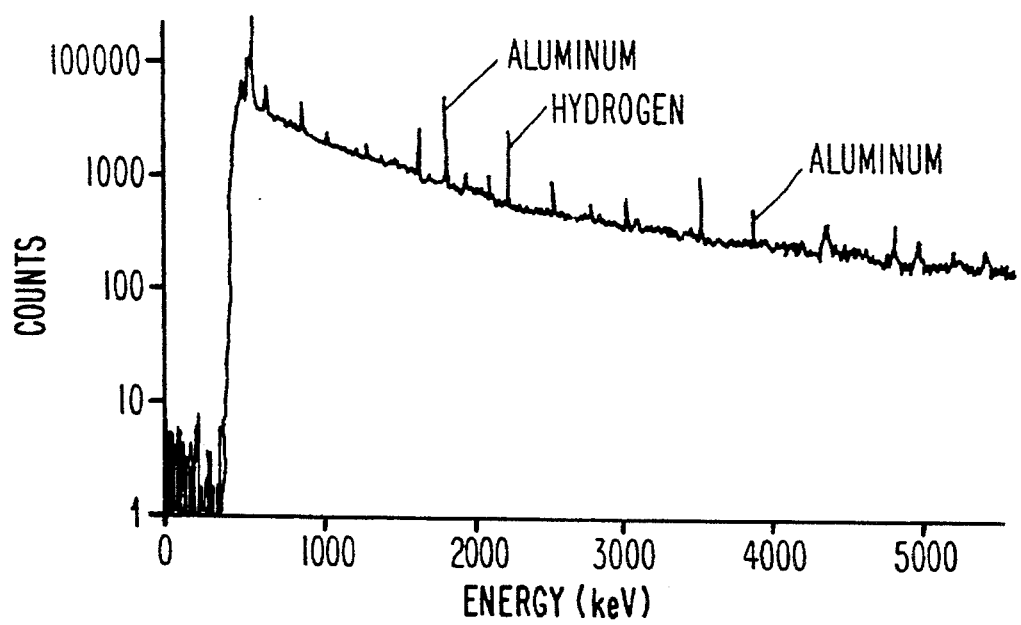

Data taken using this system is shown in FIGS. 4A and 4B. FIG. 4A depicts a series of eight gamma ray spectra, referred to as groups G1 through G8. Each group represents a spectrum of gamma rays detected during an interval of 500 microseconds. Group G1 corresponds to the neutron generator on-time, i.e., the first 500 microseconds. The following groups (Groups G2–G8) represent successive 500 microsecond intervals following the neutron generator onperiod. FIG. 4B depicts an expanded view of Group G2. Hydrogen and aluminum activation lines are identified in this figure. As mentioned above, the specific energy levels corresponding to particular elements of interest are known in advance from direct measurement or compilations of nuclear data.

III. INFERENCE OF CONTAMINATION DEPTH PROFILES

Two methods for determining the depth distribution of contaminants will now be described. The first method makes use of the known behavior of the neutron energy distribution with depth as the neutrons propagate beneath the surface; the second method makes use of the known attenuation properties of soil for gamma rays of very different energies, emitted with known yields, from the same element.

A. METHOD BASED ON SPATIAL AND ENERGY DISTRIBUTION OF NEUTRON FIELD

As mentioned above, a variety of reactions will be initiated for any given element if one employs a neutron field with fast, thermal, and intermediate neutrons. Since the prompt gamma rays are signatures of the target element and the reaction, the measured response of one of these gamma rays represents a folding of the contaminant concentration profile with the spatial distribution of neutrons whose energy is appropriate to initiate the reaction. Thus the depth distribution of a contaminant of interest can be determined if the spatial and energy distribution of the neutron field is known. In other words, since the energy of the signature gamma ray indicates both the element and the reaction that produced the gamma ray, the depth of the element can be bracketed by calculating the region of depth at which the neutron field had the energy appropriate to initiate the reaction.

Since the chemical composition, bulk density, and approximate water content of soil can be measured, it is possible to use any one of several well known, internationally recognized transport codes (e.g., DOT or MCNP) to calculate the neutron energy and spatial distribution of neutrons. One can also perform calculations for a given set of conditions, and develop empirical corrections for the key parameters, e.g., density and water content. For most soils, the relative amounts of silicon, aluminum, calcium, magnesium, potassium, and other oxides composing most of the soil mass will not significantly affect the neutron behavior (though they could produce very different responses of emitted gamma rays).

An illustration of the predictive capability of transport codes is provided by FIG. 5, which shows the depth distribution of reactions per atom per neutron predicted with a DOT calculation for a model of a large laboratory mockup of soil. The code was given response functions for several reactions, including neutron induced fission of $^{235}$U and $^{232}$Th, which, when folded with the energy spectrum of neutrons at each node in the model, produced the depth distributions shown. These particular responses were selected for two reasons:

1. They accentuate the effect of very different regimes of neutron energy; the $^{235}$U fission cross section is almost entirely thermal (neutron energy below 0.5 eV) and the $^{232}$Th cross section exhibits a neutron energy threshold of approximately 1.3 MeV.
2. The use of Solid State Track Recorders (SSTRs) containing micro deposits of $^{235}$U enabled a direct measurement of these responses as a function of depth.

FIG. 6 is a graph of experimentally measured $^{235}$U fission response and the prediction from DOT. This graph shows that the DOT model is capable of producing accurate predictions of the spatial distribution of neutrons. In practice, it would be desirable to ensure that an appropriate placement of neutron sources is made to ensure optimized lateral uniformity of the contours of neutron flux.

B. METHOD BASED ON DIFFERENTIAL ATTENUATION OF GAMMA RAYS

When a nuclear reaction occurs in a sample, prompt gamma rays of several different energies are often emitted from the sample; each has a known probability of occurrence, or branching ratio (often defined as the number of gammas of a particular energy emitted per 100 reactions). This is discussed above. Any medium through which the gamma rays travel will attenuate the gamma ray intensity to a degree that is a function of their energy. In particular, the attenuated gamma ray intensity $I(X)$ (photons/cm$^2$-sec) at a depth X in an absorbing medium, assuming a plane source of radiation of initial intensity $I_0$, is given by:

$$I(X) = I_0 e^{-\mu x}$$

where the attenuation coefficient $\mu$ is a decreasing function of photon energy. Thus, if a nucleus emits a photon of energy $E_1$ with branching ratio $B_1$ and a photon of energy $E_2$ with branching ratio $B_2$, the ratio of the respective measured yields, $Y_1$ and $Y_2$, after attenuation through a thickness X of soil, is given by:

$$R_{12} = \frac{Y_1}{Y_2} = \frac{B_1}{B_2} e^{-(\mu_1 - \mu_2)X}, \text{ where}$$

$$\mu_1 = \mu(E_1),$$

$$\mu_2 = \mu(E_2).$$

Therefore, one can determine X from the equation:

$$X = \frac{\ln(Y_1/Y_2) - \ln(B_1/B_2)}{\mu_2 - \mu_1}$$

Thus, the depth at which an emitting plane source is located can be inferred. By extending this treatment to a continuous distribution (e.g., a superposition of point sources), the appropriate software can infer bounding concentrations and spatial distributions of a contaminant element from the intensity and ratio of measured yields of gamma rays of differing energies.

EXAMPLE

Depth Inference From Yields of Two Reactions

Consider a case where thermal reactions induce two gamma peaks of energies $E_1$ and $E_2$, respectively, where $E_2 \gg E_1$ (e.g., $E_2$=4–9 MeV, $E_1$=0–1 MeV).

Step 1: Calibration

A slug of mass M is buried at several depths, including:
0 inches;

$X_1$, where $X_1$ is the deepest depth from which gamma rays of energy $E_1$ can escape the soil in sufficient numbers to be detected;

$X_2$, where $X_2$ is the deepest depth from which gamma rays of energy $E_2$ can escape the soil in sufficient numbers to be detected. Of course, $X_2$ is greater than $X_1$.

Calibration measurements determine the yield Y of gammas of $E_n$ at depth $X_i$. This yield is defined as $Y_{En}(X_i)$. Thus, $Y_{E1}(0)$, $Y_{E1}(X_1)$, $Y_{E2}(0)$, $Y_{E2}(X_1)$, $Y_{E2}(X_2)$ will be known ($Y_{E1}(X_2)$ will be zero).

The following ratios are defined:

$$R_{21}(0) = \frac{Y_{E2}(0)}{Y_{E1}(0)}$$

$$R_{21}(X_1) = \frac{Y_{E2}(X_1)}{Y_{E1}(X_1)}$$

(Note: For $E_1$ approximately equal to 1 MeV and $E_2$ approximately equal to 4 MeV, $X_1$ will be about 6 inches and $X_2$ will be about 20–24 inches.)

Step 2: Field Measurement of Gamma Ray Spectrum

The field measurement of the spectrum provides two measured yields; these are denoted $y(E_2)$ and $y(E_1)$. All yields will preferably be normalized to the number of neutrons emitted by the neutron generator; i.e., measured yields will be expressed in terms of counts per neutron.

Step 3: Depth Inference Calculation

It is important to note that the ratio $y(E_2)/y(E_1)$ will increase with depth below the surface. The location of the element of interest, in terms of a range of depths, is inferred by first answering the following two questions:

Is $y(E_2)/y(E_1) > R_{21}(X_1)$?

Is $y(E_1) > 0$?

Case 1: Element between 0 and $X_1$ and $X_1$ and $X_2$ $y(E_2)/y(E_1)$ will be greater than $R_{21}(X_1)$ and $y(E_1)$ will be greater than 0.

Case 2: Element between 0 and $X_1$ $y(E_2)/y(E_1)$ will be less than $R_{21}(X_1)$ and $y(E_1)$ will be greater than 0. If $y(E_1)$ is less than 0, the wrong element has been assumed.

Case 3: Element between $X_1$ and $X_2$ $y(E_2)$ will be greater than 0 and $y(E_1)$ will be 0.

Step 4: Equivalent Mass Calculation

Case 1: Element between 0 and $X_1$ and $X_1$ and $X_2$ $$ES_{max}(0 - X_1) = \frac{y(E_1)}{Y_{E1}(X_1)} M$$

$$ES_{min}(0 - X_1) = \frac{y(E_1)}{Y_{E1}(0)} M$$

$$ES_{max}(X_1 - X_2) = \frac{y(E_2) - y(E_1)R_{21}(0)}{Y_{E2}(X_2)} M$$

$$ES_{min}(X_1 - X_2) = \frac{y(E_2) - y(E_1)R_{21}(X_1)}{Y_{E2}(X_1)} M$$

(Note: The product $y(E_1)R_{21}(X_1)$ represents the maximum yield of $E_2$ gammas from 0 to $X_1$; $y(E_1)R_{21}(0)$ represents the minimum yield of $E_2$ gammas from 0 to $X_1$.)

Case 2: Element between 0 and $X_1$ $$ES_{max}(0 - X_1) = \frac{y(E_2)}{Y_{E2}(X_1)} M$$

$$ES_{min}(0 - X_1) = \frac{y(E_2)}{Y_{E2}(0)} M$$

Alternatively, the following equations can be used to calculate the maximum and minimum equivalent element slugs between 0 and $X_1$:

$$ES_{max}(0 - X_1) = \frac{y(E_2)}{Y_{E2}(X_1)} M$$

$$ES_{min}(0 - X_1) = \frac{y(E_2)}{Y_{E2}(0)} M$$

Case 3: Element between $X_1$ and $X_2$ $$ES_{max}(X_1 - X_2) = \frac{y(E_2)}{Y_{E2}(X_2)} M$$

$$ES_{min}(X_1 - X_2) = \frac{y(E_2)}{Y_{E2}(X_1)} M$$

($ES_{max}$ and $ES_{min}$ represent the maximum and minimum equivalent mass within the specified ranges.)

It should be noted that the maximum and minimum mass content can always be determined for two zones ($0 \leq depth \leq X_1$, $X_1 \leq depth \leq X_2$) by using two predetermined energy levels. The analysis can be extended to more zones by using more energy levels.

Next, to convert the mass content to parts per million (ppm), the calculated mass must be divided by the mass of the contributing soil. For example, this calculation can be performed by assuming that the shape of the contributing mass is a trapezoidal cylinder. The details of this calculation will be apparent or readily available to those of ordinary skill in the art.

Table 1 above lists expected counts per second for a number of elements of interest. The table assumes typical recommended "clean" levels of the elements. In addition, a typical soil slurry (1.76 gm/cc dry, 94% mass fraction powder in slurry) is assumed. Note that, for Pb, inelastic scattering of energetic neutrons is assumed, with a conservative cross section assumed for the expected energy spectrum. Thermal capture is assumed for all other elements. (This does not preclude the use of the disclosed methods and apparatus to measure the concentration profile of Pb using thermal capture.) Further, the time required to detect the assumed concentration with a standard deviation of 25%, amidst a background which is four times the true count rate, is also listed. The results listed in Table 1 demonstrate that a PGNAA system employing the neutron pulse and acquisition timing control described above is a powerful and practical tool.

IV. HIGH SENSITIVITY PGNAA

The present invention may be employed for the detection of trace elements in a sample. This capability is important for a number of applications, including in-situ PGNAA analysis of soils for trace contaminants and on-line monitoring of soil washing (see U.S. Pat. No. 5,133,901). Several modifications of the methods described above have been devised to provide a trace element analysis capability. These modifications are described below.

Except for $^4$He, all stable nuclides can capture a thermal neutron with a release of energy in the form of gamma rays. Since reaction cross sections generally increase with decreasing energy, thermal neutron capture gamma rays are usually produced in the highest yields in neutron irradiations. However, background gamma rays and gamma rays from threshold reactions and activation product radionuclides will also be present. Methods for enhancing the detection of the gamma rays of interest are required to successfully use PGNAA for trace element analysis. This is because the most abundant gamma rays will generally be produced by the most abundant elements.

The detection of particular signature gamma rays can be facilitated by exploiting the time sequence of neutron-induced reactions. Threshold reactions (fast neutron-induced reactions) occur instantaneously; that is, the gamma rays are emitted within $10^{-14}$ seconds of neutron capture (no time is required for the neutrons to be moderated to lower energies). Therefore, even with the fastest available electronics, neutrons will still be present when the gamma rays are detected. Thermal neutron-induced reactions also proceed rapidly but time is required for the neutrons to be moderated to thermal energies. Typically, the time required is on the order of 0.1–1 µs and, once formed, the thermal neutrons can have mean lifetimes of tens to hundreds of microseconds, depending on the neutron capture characteristics of the moderating media. During this time, thermal neutron-induced reactions can take place until all the neutrons are captured. Gamma rays from radionuclide production and background gamma rays will essentially be constant on a microsecond to millisecond time scale. Thus, if the nuclide of interest is to be detected via a threshold reaction, use of a pulsed neutron source and counting only during the neutron pulses will enhance detection of these gamma rays relative to thermal neutron-induced reaction gamma rays, radionuclide gamma rays, and background gamma rays. Similarly, detection of thermal neutron-induced reaction gamma rays can be enhanced by counting immediately following neutron bursts and for a duration of hundreds of microseconds.

High-speed detection electronics are required to exploit the time sequence of neutron-induced reactions and obtain increased gamma ray detection sensitivities. In a standard High-Purity Germanium (HPGe) gamma ray detection system, count rate throughput is controlled by:

(1) charge collection times for pulses produced by gamma rays in the HPGe detector;

(2) pulse handling characteristics of the preamplifier;

(3) pulse handling characteristics of the amplifier;

(4) speed of the analog-to-digital converter (ADC); and (5) storage time of the multichannel pulse height analyzer.

The system amplifier presents the most serious bottleneck to count rate throughput. However, if the HPGe detector is equipped with a high-speed transistor reset preamplifier and an advanced ADC (either fixed conversion time or Wilkinson-type) is used, count rate throughputs of up to 100,000 counts per second (cps) are attainable.

At a count rate throughput of 100,000 cps, the system dead time (i.e., the time required for the electronics to process pulses) will be 60–80% of the clock time, depending on spectrum characteristics. Therefore, a pulsed neutron generator with extended neutron pulse duration is employed to decrease the neutron intensity per unit time and thereby enhance detection of gamma rays from fast neutron-induced reactions. The neutron generator produces neutron bursts with durations in the 100–700 µs range. The neutron output of this generator is about $5 \times 10^7$ neutrons/cm$^2$/second. Control of the generator is accomplished through an acquisition interface module (AIM).

The AIM is designed to run the neutron generator at a preselected pulse length and frequency while at the same time controlling the multichannel analyzer (MCA) to obtain gamma ray spectra for predetermined acquisition periods synchronized with the operation of the neutron generator. Thus, for example, the neutron generator may be run for 200 µs while the MCA obtains a synchronized 200 µs spectrum followed by a series of seven 400 µs spectra. Fast neutron-induced reaction gamma rays would be detected only in the first counting interval whereas thermal neutron-induced reaction gamma rays would be detected mainly in the first four groups. Background gamma rays and gamma rays emitted by radionuclides produced by neutron activation would be detected with equal probability in all eight intervals.

Figure 7:
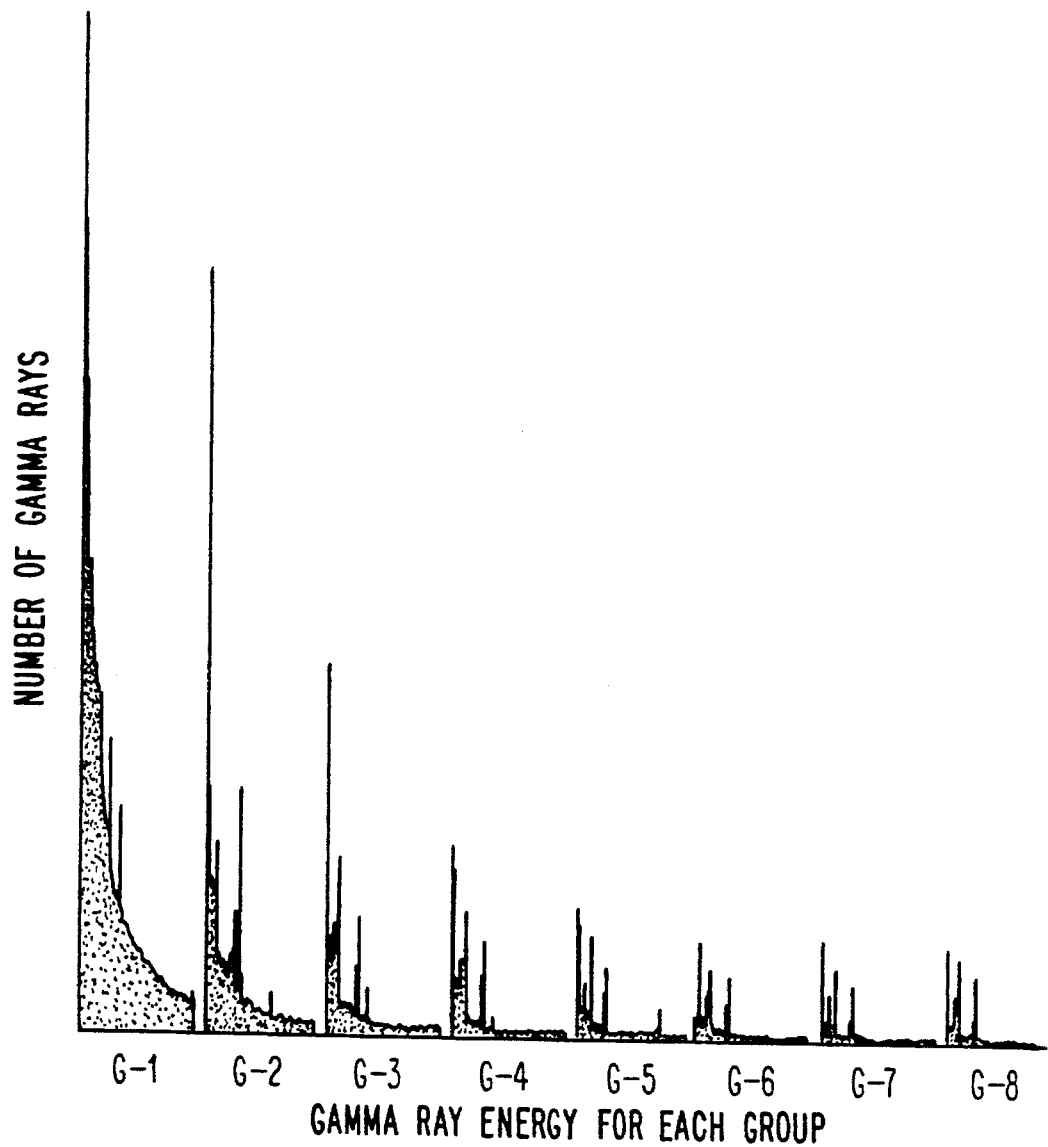
FIG. 7 depicts exemplary gamma ray spectra obtained in accordance with another embodiment of the present invention.

FIG. 7 depicts an example of high-sensitivity PGNAA data acquired with high-speed timing techniques. The neutron generator was run for 500 µs at a rate of 200 pulses per second. Each spectrum corresponds to a counting period of 250 µs. The first two spectral groups are thus encompassed by the generator-on period.

Gamma rays from fast neutron-induced reactions appear only in the first two groups (i.e, the first two spectra), which contain many more counts than the following six groups. Both groups taken with the neutron generator on correspond to very high dead times (high count rate losses). Although thermal neutron-induced reaction gamma rays are present in the first two groups, their intensity is low because of losses and the fact that the thermal neutron reaction rate had not yet peaked. A prominent peak in the spectra, at 2223 keV, is a consequence of the capture of thermal neutrons by hydrogen. FIG. 8 shows a plot of the intensity of the 2223 keV gamma rays for each of the spectral groups. The maximum count rate occurs in group 3 (the first 250 µs after the neutron pulse ended), and the intensity falls off exponentially with time in the next few groups. The remaining signal in groups 7 and 8 is due to so-called "wall return" thermal neutrons. (Wall return is a laboratory effect.) The intensity of the 2223 keV gamma rays decreases by a factor of 2 every 150 µs, a rate that is determined by the neutron capture characteristics of the thermalizing medium, which in this case was soil below the neutron generator. Groups 7 and 8 contain mainly "long-lived" gamma rays from background and from nuclides produced in neutron activation (such as $^{16}N$ with a half life of 7 seconds produced by the $^{16}O(n,p)^{16}N$ reaction on oxygen in the soil). These gamma rays are present at equal intensity in all of the groups.

It can be seen that use of the data from groups 1 and 2 will result in much better sensitivity for fast neutron-induced reactions because only the background that occurs in the narrow time interval corresponding to the generator-on period is encountered. Similarly, maximum sensitivity for neutron capture gamma rays results from summing the data in groups 3 and 4.

The methods described herein offer a number of improvements to the basic PGNAA technique, including:

(1) increased sensitivity due to higher count rate input;
(2) increased sensitivity due to detection of reaction gamma rays during the time interval in which they occur (i.e., increased signal-to-background); and
(3) separation of gamma ray events from different types of reactions. Fast neutron-induced reactions and thermal neutron-induced reactions will occur with different spatial distributions in the sample. For example, if 14 MeV neutrons are being attenuated by a solid such as soil, the fast neutron flux will drop off exponentially with distance from the surface of the sample, whereas the thermal neutron flux will increase and reach a maximum roughly six to ten inches from the surface.

Thus, different portions of a nonhomogeneous sample can be sampled simultaneously.

The sensitivity of the method may be further enhanced by the addition of an anti-Compton suppression ring of detectors around the HPGe detector(s). These improvements to PGNAA make possible the use of the technique for trace element analysis.

V. PGNAA SYSTEM FOR ANALYSIS OF MAJOR AND TRACE COMPONENTS OF OBJECTS, PACKAGES OR FLOW STREAMS

The methods discussed above are useful for analyzing liquids, soil slurries, powders, solid objects, soil cores, and packages of various sizes. In addition, the system is transportable so that, if needed, it could be assembled onsite at a remote facility to characterize suspect samples without shipping the samples offsite. Further, as discussed above, the system is capable of real-time measurement and providing results within minutes.

Assume, e.g., that the system has an interrogation volume of one cubic foot and that, using a 14 MeV tube source, the moderating material produces within the interrogation volume a thermal neutron flux of $10^7$ neutrons/$cm^2$-sec and a flux of E>1 MeV neutrons of $10^7$ neutrons/$cm^2$-sec. Further, assume that there are two high purity germanium detectors respectively placed on opposite faces of the interrogation volume. The following table lists expected counts per second from each listed element, at typical recommended "clean" levels in soil. A typical soil slurry (1.76 gm/cc dry, 94% mass fraction powder in slurry) is assumed for this illustration. Note that, for Pb, inelastic scattering of energetic neutrons is assumed, with a conservative cross section assumed for the expected energy spectrum. Thermal capture is assumed for all other elements (more recently obtained data indicate that thermal neutron capture for Pb may lead to lower detection limits for this element). In addition, the time required to detect the assumed concentration with a standard deviation of 25%, amidst a background which is four times the true count rate, is also listed.

TABLE 2

| Element | ppm in soil by mass | Expected counts/sec | Counting time (sec) |
|---|---|---|---|
| Cl | 300 | 18.3 | 7.9 |
| Cu | 250 | 0.8 | 180 |
| Cd | 10 | 1.1 | 131 |
| Fe | 300 | 1.1 | 131 |
| Hg | 2 | 0.4 | 360 |
| Ni | 300 | 1.5 | 96 |
| Pb | 50 | 0.2 | 720 |
| Th | 105 | 0.7 | 206 |
| U | 42 | 0.2 | 720 |

Table 2 demonstrates that a system based on PGNAA with the neutron pulse and acquisition timing control described above can be used as a practical tool for the measurement of concentrations of hazardous elements in a variety of samples and geometries. Such a system will also use neutron doses which are so low (typically less than $10^{12}$ neutrons) that post-irradiation residual radioactivity will not be a problem.

In summary, PGNAA can be used as a real time method for determining the depth distribution of hazardous elements in a field of soil. Using successive measurements over a field with three different neutron generator tube configurations (DT, DD, and DD with above ground thermalization), one can achieve a depth distribution due to the three respective average depths of neutron thermalization these sources provide. In addition, using a DT source of 14 MeV neutrons, there will be sufficient neutron energy to excite inelastic scattering and other "fast neutron" reactions, which also produce distinct signature gamma rays of high energy. These additional gamma rays can enhance the depth profile information, according to the region of soil depth at which the neutron average energy is above the neutron energy thresholds of the respective reactions. Utilizing measured ratios of gammas of different energies produced by the same nuclide further enhances the depth profile information because of the different attenuation of intensity experienced by the different energy gamma rays. A three region depth profile of a 50 ft. by 50 ft. area can be produced in approximately thirty hours of interrogation time using a system including two neutron tube sources, six germanium detectors covering a 6 ft. by 3 ft. ground surface, and an online computer analysis system. Larger systems will provide commensurately lower survey times. The systems described above may also be employed to detect trace elements.

We claim:

1. A method for analyzing an interrogation volume containing a prescribed target element, comprising the steps of:

(a) irradiating an interrogation volume with a neutron burst characterized by an intensity and pulse width, and thereby effecting an emission of gamma radiation from said interrogation volume;

(b) acquiring groups of gamma radiation data during a plurality of time intervals, each group being indicative of the number or intensity of gamma rays and energy levels of said gamma rays during a corresponding time interval, and a first group corresponding to a first interval during which said neutron burst is on, and at least one other group corresponding to a time interval during which said neutron burst is off; and (c) analyzing said gamma data to detect the presence and determine the amount of said prescribed target element in said interrogation volume and to determine whether said prescribed target element is present within a prescribed depth range in said interrogation volume; and (d) determining calibration data by carrying out the following sub-steps:

(1) placing a slug of mass M of said target element at a plurality of depths, including: 0 inches; $X_1$, where $X_1$ is the deepest depth from which gamma rays of energy $E_1$ can escape the interrogation volume in sufficient numbers to be detected; and $X_2$, where $X_2$ is the deepest depth from which gamma rays of energy $E_2$ can escape the interrogation volume in sufficient numbers to be detected; and measuring yields $Y_{E1}(0)$, $Y_{E1}(X_1)$ of gamma rays of energy $E_1$ at depths of 0 inches and $X_1$, respectively, and $Y_{E2}(0)$, $Y_{E2}(X_1)$, $Y_{E2}(X_2)$ of gamma rays of energy $E_2$ at depths of 0 inches, $X_1$ and $X_2$, respectively;

(2) defining the following ratios:

$$R_{21}(0) = \frac{Y_{E2}(0)}{Y_{E1}(0)}$$

$$R_{21}(X_1) = \frac{Y_{E2}(X_1)}{Y_{E1}(X_1)}$$

performing a field measurement of yields $y(E_1)$, $y(E_2)$ of gamma rays of energies $E_1$, $E_2$, respectively;

performing a depth inference calculation by determining whether $y(E_2)/y(E_1)$ is greater than $R_{21}(X_1)$ and whether $y(E_1)$ is greater than 0, and then determining a range of depths at which said target element is located by the following formulas:

Case 1 if $y(E_2)/y(E_1)$ is greater than $R_{21}(X_1)$ and $y(E_1)$ is greater than 0, then the target element is present between 0 and $X_1$ and between $X_1$ and $X_2$;

Case 2 if $y(E_2)/y(E_1)$ is less than $R_{21}(X_1)$ and $y(E_1)$ is greater than 0, then the target element is between 0 and $X_1$;

Case 3 if $y(E_2)$ is greater than 0 and $y(E_1)$ is 0, then the target element is between $X_1$ and $X_2$; and then, performing an equivalent mass calculation by the following formulas:

Case 1

$$ES_{max}(0 - X_1) = \frac{y(E_1)}{Y_{E1}(X_1)} M$$

$$ES_{min}(0 - X_1) = \frac{y(E_1)}{Y_{E1}(0)} M$$

$$ES_{max}(X_1 - X_2) = \frac{y(E_2) - y(E_1)R_{21}(0)}{Y_{E2}(X_2)} M$$

$$ES_{min}(X_1 - X_2) = \frac{y(E_2) - y(E_1)R_{21}(X_1)}{Y_{E2}(X_1)} M$$

Case 2

$$ES_{max}(0 - X_1) = \frac{y(E_2)}{Y_{E2}(X_1)} M$$

$$ES_{min}(0 - X_1) = \frac{y(E_2)}{Y_{E2}(0)} M$$

or, $$ES_{max}(0 - X_1) = \frac{y(E_2)}{Y_{E2}(X_1)} M$$

$$ES_{min}(0 - X_1) = \frac{y(E_2)}{Y_{E2}(0)} M$$

Case 3

$$ES_{max}(X_1 - X_2) = \frac{y(E_2)}{Y_{E2}(X_2)} M$$

$$ES_{min}(X_1 - X_2) = \frac{y(E_2)}{Y_{E2}(X_1)} M$$

wherein $ES_{max}$ and $ES_{min}$ represent the maximum and minimum equivalent mass within the specified ranges;

wherein steps a, b, and c are performed with a neutron source, detector and analysis system, respectively, wherein said neutron source, detector and analysis system are maintained outside said interrogation volume and in a non-contacting relation with said target element.

2. The method recited in claim 1, wherein said pulse width is approximately 100–500 µs.

3. The method recited in claim 1, wherein said plurality of time intervals spans approximately 5000 µs.

4. The method recited in claim 1, wherein step (a) comprises generating neutrons with energies of approximately 14 MeV.

5. The method recited in claim 1, wherein step (a) comprises generating neutrons with energies of approximately 3 MeV.

6. The method recited in claim 1, wherein step (a) comprises generating neutrons with energies of approximately 0.025 eV.

7. The method recited in claim 1, wherein step (a) comprises generating neutrons with energies of approximately 750 keV.

8. The method recited in claim 1, wherein said analyzing step for determining whether said target element is present within a first prescribed depth range comprises the step of computing a depth at which said neutrons have energy appropriate to initiate a reaction that produces gamma radiation indicative of said target element.

9. The method recited in claim 1, further comprising the step of generating depth profile data representing the amount of said target element at a plurality of depth ranges in said interrogation volume.

10. The method recited in claim 1, wherein said target element is a soil contaminant.

11. The method recited in claim 1, wherein said target element is a member of a group consisting of uranium, thorium, cadmium, and copper.

12. The method recited in claim 1, wherein said target element is a member of a group consisting of Cl, Cu, Cd, Fe, Hg, Ni, Pb, Th, and U.

\* \* \* \* \*